United States Patent [19]

Naser et al.

[11] Patent Number: 5,018,724
[45] Date of Patent: May 28, 1991

[54] ARRANGEMENT FOR MEASURING PHYSIOLOGICALLY GENERATED WEAK BIOMAGNETIC SIGNALS WHILE THE EXAMINATION SUBJECT IS AT REST AND EXERCISING

[75] Inventors: Georg Naser, Zirndorf; Siegfried Schneider, Erlangen, both of Fed. Rep. of Germany

[73] Assignee: Siemens Aktiengesellschaft, Munich, Fed. Rep. of Germany

[21] Appl. No.: 426,978

[22] Filed: Oct. 26, 1989

[30] Foreign Application Priority Data

Nov. 28, 1988 [EP] European Pat. Off. ........... 88119825

[51] Int. Cl.$^5$ ....................... A63B 21/00; A61B 6/00
[52] U.S. Cl. ........................................ 272/73; 272/129; 272/DIG. 6; 128/659; 128/653 R
[58] Field of Search ............ 272/73, DIG. 5, DIG. 6, 272/72; 128/653, 707, 659

[56] References Cited

U.S. PATENT DOCUMENTS 3,767,195 10/1973 Dimick .
4,632,123 12/1986 Govaert et al. ....................... 272/73
4,801,882 1/1989 Daalmans ............................ 128/653

FOREIGN PATENT DOCUMENTS 0277283 10/1987 European Pat. Off. .

OTHER PUBLICATIONS

Zimmerman (Journal of Applied Physics)-American Institute of Physics. Title: "Squid Instruments and Shielding for Ion Lever Mag. Measurements", Feb. 1977.
Best Bets-Pumping Iron-California Magazine, 11-1985, p. 138; Cl272/72, Biomedizinische Technik-"EKG Mapping", Nov. 1980, pp. 285-292.
Quinton Instruments Catalog, Jul. 1, 1974, p. 18, Bike Ergometer.
"Magnetic Measurements of Cardiac Mechanical Activity," Maniewski et al., IEEE Trans. on Biomed. Eng., vol. 35, No. 9, Sep. 1988, pp. 662-669.
"Body Surface Mapping During Exercise in the Diagnosis of Coromary Heart Disease," Hinsen et al., Biomed. Techn., vol. 25, No. 11, 1980, pp. 285-292.
"MCG Inverse Solution: Influence of Coil Size, Grid Size, Number of Coils, and SNR," Abraham-Fuchs et al., IEEE Trans. on Biomed. Eng., vol. 35, No. 8, Aug. 1988, pp. 573-575.

Primary Examiner—Stephen R. Crow
Attorney, Agent, or Firm—Hill, Van Santen, Steadman & Simpson

[57] ABSTRACT

A multi-channel arrangement for measuring weak magnetic fields in living tissues, and for localizing the current sources which cause the magnetic fields by evaluating the topical magnetic values measured by individual sensors of the apparatus mounted in a vertically adjustable fashion to a patient support, the patient support being longitudinally and transversely adjustable, has a bicycle ergometer disposed at a foot end of the patient support, the bicycle ergometer consisting exclusively of components which are nonmagnetic and which do not generate a magnetic field. The bicycle ergometer is used by an examination subject so that signals can be obtained by the subject at rest and at a defined exertion level. The bicycle ergometer is mounted and constructed so that the examination subject can operate the ergometer after being positioned in a fixed position on the support.

3 Claims, 1 Drawing Sheet

ARRANGEMENT FOR MEASURING PHYSIOLOGICALLY GENERATED WEAK BIOMAGNETIC SIGNALS WHILE THE EXAMINATION SUBJECT IS AT REST AND EXERCISING

BACKGROUND OF THE INVENTION

1. Field of the Invention

The present invention is directed to an apparatus for measuring weak biomagnetic fields which are physiologically generated by an examination subject, the biomagnetic fields appearing topically and chronologically in the body of a patient, and in particular to an apparatus which permits such fields to be measured while the patient is in an exercise condition and in a resting condition.

2. Description of the Prior Art

It is known to measure the chronological course of electrical pulses emanating from the beating heart using electrodes applied to specific locations on the body surface, and to record this signal in an electrocardiogram. Frequently such measurements are undertaken with the patient being at rest and exercising, so as to obtain an "at rest" ECG and an exercise ECG. The latter measurement is taken immediately after the patient has undergone defined physical exercise, usually using an ergometer so that the exercise level can be recorded. Because the electrodes affixed to the body are connected to the ECG measuring instrument via flexible lines, these measurements are independent of the position and movements of the body during each measurement.

Electrocardiograms produced in this manner are diagnostically valid with respect to the amplitude and frequency of the pulses which are generated by the heart. Such electrocardiograms are not suitable, however, for localizing specific electrical events occurring in the heart muscle, and thus cannot be used to provide conclusive information as to the spatial position of electrical events and their chronological course.

It is also known to employ magnetic methods for measuring and analyzing local bioelectrical currents in the biological tissue complexes, particularly the brain and the heart, and to perform such and measurements so as to produce magneto-encephalograms (MEG) and magneto-cardiograms (MCG).

A known apparatus which is suitable for this purpose is described in an article entitled "Biomagnetismus" by Hohnsbein in the periodical Bild der Wissenschaft, No. 8, 1986, pages 76–83. This known apparatus is capable of measuring extremely weak biomagnetic signals, for example, the magnetic fields which arise in living tissue complexes due to directed current flows, having a field strength on the order of magnitude of $10^{-12}T$ and below. These signals can be measured only by special sensor arrangements when the patient and measuring equipment are carefully shielded from external magnetic fields. The sensor arrangement consists of a plurality of measuring devices known as gradiometers so that an exact localization of the current source in the tissue can be identified. These gradiometers are coupled to a corresponding number of SQUIDs (superconducting quantum interference devices). Both the gradiometer and the associated SQUID must be accommodated in a cryostatic temperature regulator, in which a temperature prevails at which the SQUID and the gradiometer are superconducting. The error with which the current source can be localized has a defined relationship to the number of sensors, i.e., to the number of measuring points, as explained in the article "MCG Inverse Solution, Influence of Coil Size, Gride Size, Number of Coils, and SNR," Abraham-Fuchs, IEEE Transactions on Biomedical Engineering, Vol. 35, No. 8, August 1988, pages 573–575, particularly section C of that article in combination with FIG. 5 of the article. In order to obtain a localization error which is sufficiently low for clinical use, the magnetic signals must be simultaneously measured with at least 10 to 12 channels dependent on the signal-to-noise ratio.

Among other reasons, because of their low temperatures, magnetic sensors, differing from ECG electrodes, can not be affixed to the body of the patient and connected to a central unit via flexible lines. By contrast, these magnetic sensors must be arranged at a specified distance from the examination subject. This means that the body of the examination subject cannot change spatially relative to the magnetic sensors during a measuring event. This means that the body of the patient must be situated in a fixed position relative to the magnetic sensors, including the time when measurements are undertaken after exertion on the part of the patient. It is necessary to undertake an exercise measurement immediately after the exertion by the patient insofar as possible. Consequently, it is not possible to lead the patient to a support table after the ergometer exertion, and to affix the patient at that location in order to subsequently register the MCG. The time which passes would be too long to permit a diagnostically relevant exercise measurement to be taken.

In other medical areas, it is known to provide an exercise mechanism at the foot end of a patient's bed, to permit the bed-ridden patient to avoid the formation of embolisms after an operation. Such exercise equipment, however, does not include an ergometer which permits a diagnostically relevant measurement of an exercise ECG or an exercise MCG to be taken.

SUMMARY OF THE INVENTION

It is an object of the present invention to provide an apparatus wherein an exercise magnetocardiogram can be made immediately after a defined exertion by an examination subject, without relocating the patient and without the influence of external magnetic fields or distortions of the biomagnetic field.

The above object is achieved in accordance with the principles of the present invention in a multi-channel arrangement for measuring weak magnetic fields in living tissue and for localizing the current sources causing the magnetic fields wherein an ergometer is rigidly mounted at the foot end of a patient support, the patient support being longitudinally and transversely adjustable and the magnetic measuring arrangement being vertically adjustable. The patient can operate the ergometer after the patient has been positioned in a fixed location on the support. Magnetic field measurements can then be taken while the patient is at rest and while, or immediately after, the patient is in an exercise mode. The ergometer consists exclusively of components which are nonmagnetic and which do not generate a magnetic field.

In a preferred embodiment, the ergometer is a bicycle ergometer having an adjustable strap brake so that a defined torque for the flywheel, which is operated by the patient, can be set and recorded.

In a further embodiment the biomagnetic measuring system can be augmented by an ECG measuring system.

The ergometer is preferably readily detachable from the patient support table.

DESCRIPTION OF THE PREFERRED EMBODIMENTS

Figure 1:
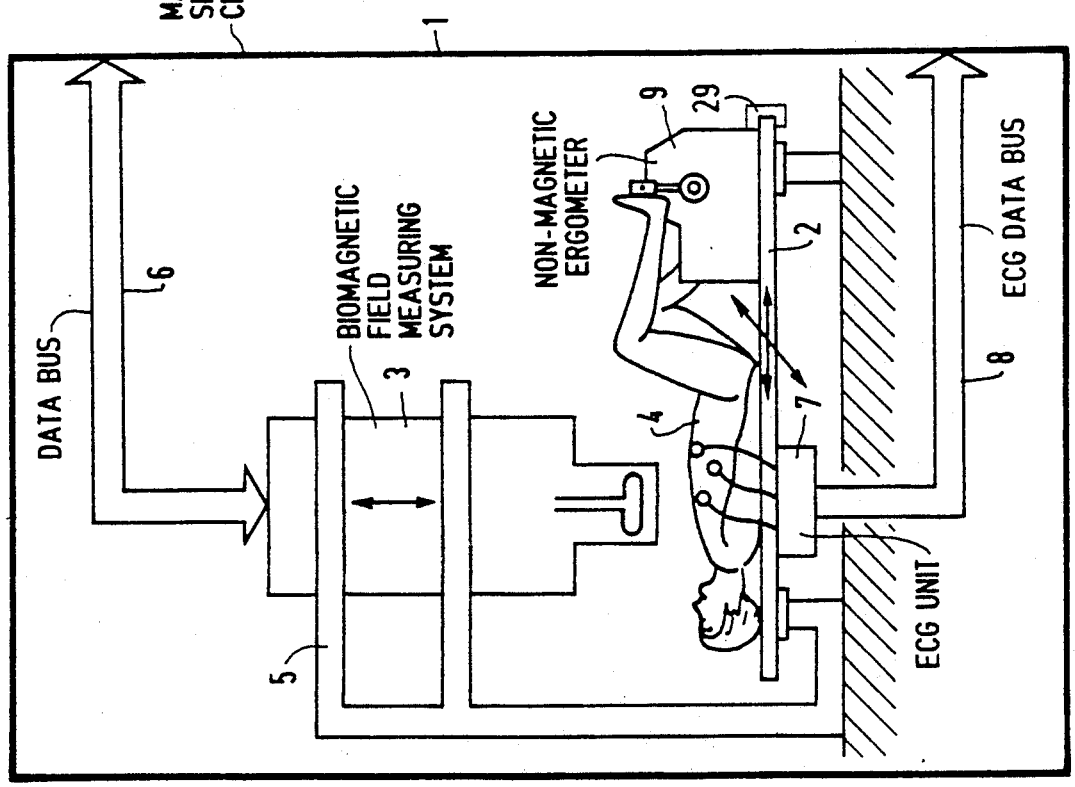
FIG. 1 is a schematic diagram showing a measuring arrangement, including an ergometer, constructed in accordance with the principles of the present invention.

A measuring apparatus constructed in accordance with the principles of the present invention is shown in FIG. 1. The apparatus includes a magnetically shielded chamber 1 in which a patient support platform or table 2 is disposed together with a measuring arrangement 3, of known construction, for measuring biomagnetic fields emanating from a patient 4 lying on the patient support 2 in the measurement volume ("field of view") of the measuring arrangement 3. The measuring arrangement 3 is attached to a mounting frame 5 so as to be vertically adjustable, the mounting frame 5 being mechanically connected to the patient support 2. The measuring apparatus 3 is connected via a data bus 6 to a system (not shown) of known construction for the evaluation and portrayal of the measured data in the form of a magneto-cardiogram (MCG). In addition, an ECG system 7 can also be provided, so that ECG data are also available in addition to the MCG data. The ECG signals proceed via an ECG data bus 8 to an ECG registration unit (not shown). A bicycle ergometer 9 is detachably mounted to the foot end of the patient support 2 by a releasably holding element 29, such as a clamp, bolts or other suitable means. The ergometer 9 is arranged on the support 2, so that the patient 4 can operate the ergometer 9 while lying down, and without changing position from an "at rest" position.

Figure 2:
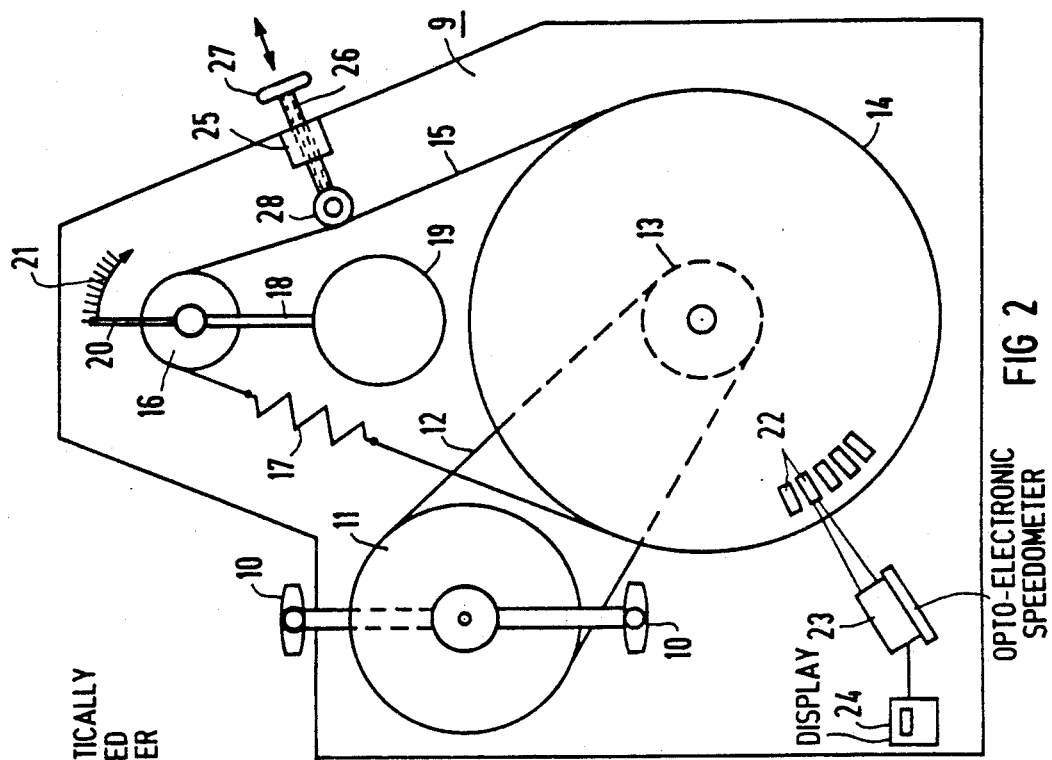
FIG. 2 is a side view of the internal components of the ergometer shown in FIG. 1.

The internal components of the bicycle ergometer 9 are shown in FIG. 2. This basic structure may be of the type as is known for use in exercise equipment (except for component composition, as described below). A drive wheel 11 which is operable by pedals 10 is connected via a drive belt 12 to the axle 13 of a flywheel 14. The circumference of the flywheel 14 is entrained by a brake strap 5 which subtends a defined angle. The brake strap 15 is conducted around the outside of a pendulum roller 16 and is tensed by a tension spring 17. The pendulum roller 16 is connected by a pendulum rod 18 to a weight 19. The weight 19, dependent on the tangential frictional forces acting on the pendulum roller 16, given movement of the flywheel 14, is moved opposite to the effective direction of the tangential force. The weight 19 will thus be moved through an angle around the pivot point of the pendulum roller 16, dependent on this tangential force. The pendulum angle is thus a measure of the power exerted on the flywheel 14. The pendulum rod 18 is provided with an indicator rod 20, which extends beyond the outer diameter of the pendulum roller 16. The point of the indicator rod 20 points to a value on an indicator scale 21, calibrated in watts, and which is a measure of the power being exerted by the patient in rotating the flywheel 14.

The flywheel 14 has a plurality of reflectors 22, constructed similar to a gear rim. A light ray from an optoelectronic speedometer 23 is directed onto the reflectors 22. The reflected light as measured by the speedometer 2 identifies the speed per time unit of the flywheel 14 on the basis of the number of light pulses reflected per time unit. An electrical signal corresponding to the speed is supplied to a display 24.

To set the magnitude of a desired exertion of the patient within a broad range of exertion, an exertion setting system is provided which acts on the brake strap 15 such that the gripping power of the brake strap 15 can be continuously increased from a minimum value to a maximum value. The exertion setting system includes a threaded spindle 26 rotatably seated in a threaded bushing 25, so that the spindle 26 can be inwardly or outwardly advanced so as to increase or decrease lateral pressure applied to the brake strap 15 via a roller 28 at an end of the spindle 26. The gripping power (i.e., frictional interaction) of the brake strap 15 relative to the flywheel 14 can thereby be adjusted by rotating a handle 27 at the opposite end of the spindle 26.

In order to obtain reliable biomagnetic measurements, it is important that the ability of the measuring apparatus to identify the spatial position and chronological course of the bioelectric current sources, which generate the measured biomagnetic fields, not be impaired. It is thus important that the ergometer 9 not provide any external magnetic fields which can disturb such a measurement. Conventional bicycle ergometers having a structure similar to that described above, which are used for exercise purposes, consist largely of ferromagnetic materials. It is thus important for the apparatus disclosed and claimed herein that the ergometer 9 be exclusively constructed of non-magnetic materials. The components may consist, for example, of aluminum, bronze, organic plastics and non-magnetic steel. It is also important that the measuring devices for the power and speed do not produce any electromagnetic fields.

Although modifications and changes may be suggested by those skilled in the art, it is the intention of the inventors to embody within the patent warranted hereon all changes and modifications as reasonably and properly come within the scope of their contribution to the art.

We claim as our invention:

1. An apparatus for measuring weak biomagnetic fields comprising:

magnetic field measuring means for measuring, within a measuring volume, weak biomagnetic fields and for identifying the topical distribution and chronological course of bioelectric current sources which generate said biomagnetic fields;

support means adapted to support a patient in a fixed position within said measuring volume of said magnetic field measuring means; and bicycle ergometer means mounted on said support means and adapted to be operated by a patient for exercising said patient in said fixed position on said support means so that a measurement can be made by said magnetic field measuring means with said patient at rest in said fixed position and after operation of said ergometer means in said fixed position, said ergometer means consisting exclusively of components which are non-magnetic and which do not generate a magnetic field, said bicycle ergometer means having a fly wheel adapted to be rotated by said patient, a strap brake surrounding said fly wheel, means mechanically interacting with said fly wheel for measuring and displaying the mechanical power exerted by a patient in rotating said fly wheel, and opto-electronic speedometer means optically interacting with said fly wheel for measuring and displaying the speed of said fly wheel.

2. An apparatus as claimed in claim 1, further comprising:

ECG means adapted for connection to said patient in said fixed position on said support means for providing an ECG measurement of said patient.

3. An apparatus as claimed in claim 1, further comprising means for detachably mounting said bicycle ergometer means to said support means.

* * * * *